Figure 1:
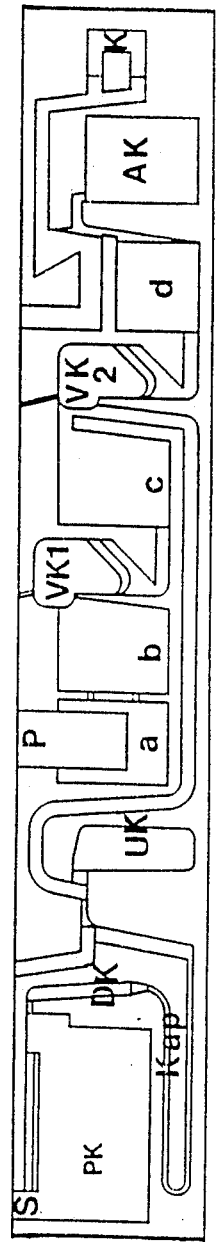

United States Patent [19]

Kaspar

[11] Patent Number: 4,880,731
[45] Date of Patent: Nov. 14, 1989

[54] PROCESS AND REAGENT FOR THE DETERMINATION OF A REACTION PARTNER OF AN IMMUNOLOGICAL REACTION

[75] Inventor: Klaus P. Kaspar, Asuncion, Paraguay

[73] Assignee: Boehringer Mannheim GmbH, Mannheim, Fed. Rep. of Germany

[21] Appl. No.: 25,876

[22] Filed: Mar. 16, 1987

[30] Foreign Application Priority Data

Mar. 19, 1986 [DE] Fed. Rep. of Germany ....... 3609217

[51] Int. Cl.⁴ ................. G01N 33/543; G01N 33/547; G01N 33/535
[52] U.S. Cl. ....................................... 435/7; 436/512; 436/518; 436/523; 436/531; 436/532; 436/533; 436/540; 436/809; 436/819; 436/825; 436/826
[58] Field of Search ............... 436/531, 532, 533, 518, 436/523, 512, 809, 819, 825, 826, 540; 435/7

[56] References Cited

U.S. PATENT DOCUMENTS

| | | | |
|---|---|---|---|
| 4,320,109 | 3/1982 | Wolf et al. | 421/1 |
| 4,467,031 | 8/1984 | Gallati et al. | 435/7 |
| 4,535,057 | 8/1985 | Dreesman et al. | 435/5 |
| 4,729,961 | 3/1988 | Avrameas et al. | 436/501 |
| 4,791,056 | 12/1988 | Sizto et al. | 435/7 |

Primary Examiner—Christine M. Nucker
Assistant Examiner—D. John Griffith, Jr.
Attorney, Agent, or Firm—Felfe & Lynch

[57] ABSTRACT

For the determination of a reaction partner of an immunological reaction according to the principle of immunoassay, the reaction partner to be determined is brought into contact with a marked specific receptor $R_1$ and at least 1 unmarked receptor $R_2$, one of the unmarked receptors $R_2$ being bonded on a solid phase by a binding-capable substance $R_3$. In order to determine the sample blank value, the unmarked receptor $R_2$, which is bonded by the receptor fixed on the solid phase, is then replaced by another unmarked receptor $R'_2$ which does not react with the reaction partner of $R_2$ to be determined.

9 Claims, 1 Drawing Sheet

PROCESS AND REAGENT FOR THE DETERMINATION OF A REACTION PARTNER OF AN IMMUNOLOGICAL REACTION

The invention concerns a process for the determination of a reaction partner in an immunological reaction, wherein the reaction partner to be determined is brought into contact with a marked specific receptor $R_1$ and with at least one unmarked receptor $R_2$, in which one of the unmarked receptors $R_2$ is bound to a solid phase by means of a substance $R_3$ having binding properties.

For the determination of a reaction partner of an immunological reaction, which hereinafter is also designated an analyte, use is frequently made of sandwich immunoassays. In these, a reaction partner is reacted with a receptor specific to it which is labelled in a known manner, and the complex of the reaction partner and marked receptor is reacted with a further receptor which is directed against the reaction partner to be determined or the complex, and which is fixed to a solid phase. This principle admits of further variations, in which the sequence of these reaction steps can be varied at the discretion of the user. Thus, the reaction partner can be reacted with a soluble, unlabelled and a soluble labelled receptor which are directed against the reaction partner to be determined (analyte) and the complex of the three components is then reacted with an insoluble receptor, i.e., a receptor bound to a solid phase, which is directed against the unmarked receptor.

The reaction with all three receptors can be carried out simultaneously or in stages. In all these processes, the amount of marked receptor bound to the solid phase or the amount of marked receptor which is not bound and therefore is present in the solution is determined by suitable measurement processes and is related to the amount of the reaction partner to be determined.

Examples of the label include radioactive substances, enzymes, and fluorescent or colored substances. The labelled receptor can then be determined by the alteration of the fluorescence property, development of a colored reaction product or by the distribution of radioactive substances between the solid and liquid phases. In addition, from the alteration of the measurement signal either the amount of reaction partner to be determined is computed directly, (when there is adequate theoretical knowledge of the connection between the measuring signal and the amount). Alternately, using a calibration curve, an amount of analyte is correlated to a signal. What is important in both processes is that to every alteration of the signal an amount corresponds to an amount of reaction partner.

In immunoassays of this type, however there is a problem in that unspecific accumulation occurs on the solid phase. This accumulation is caused by sample-specific influences and is termed the "matrix effect". Because even unbound labeled receptors accumulate on the solid phase, the measurement signal is falsified and hence so are the measurement results. In order to correct this error, a sample blank value must be determined. The determination of the sample blank value, however, has led until now to difficulties in cases when samples which are definitely analyte free cannot be obtained, or when no absolute measurement reference method exists for the determination of the presence or absence of the analyte in the sample. In these cases, it has been necessary in order to determine the sample blank value correctly that both the sample and the standard should behave identically. In immunological determination methods, however, this is only possible when the same material is used. For example, in determining analytes in sera it was proposed that for the preparation of a standard, serum pools should be used from which the analyte content had been removed by chemical, physical or immunological methods. The disadvantage of this process is that it is not possible to control whether analyte removal has been completely successful, because no measurement values are available for a "zero point". On the other hand, however, even with complete analyte removal a change in the sample blank value must be expected, because the removal of the analyte residue content effects a change in the matrix, which in turn can influence the calibration curve zero point and the steepness of the calibration curve. Without the knowledge of the sample blank value which has possibly changed after treatment, exact determination of the analyte residue value is not possible. Moreover, greater blank value fluctuations must be expected when using sample materials with strongly fluctuating composition, for example, when using tissue homogenates.

It was also proposed than an artificially composed material, such as buffer solutions, beef serum albumin solutions etc., should be used.

Such solutions often show different behavior from that of the sample to be tested and therefore they lead to falsified results (I. Marschner et al., Journal of Clinical Chemistry and Clinical Biochemistry, 1976, 345-351).

At present no process is yet known which can measure, for example, serum-specific sample blank values in varying human serum samples. The consequence is that for all such samples a common hypothetical blank value must be assumed. Inevitably, every signal difference against this blank value must be attributed to analyte content, although the signal may just as well have been caused by specific properties of the sample.

As of now there is still no process by which it is possible to produce an analyte-free matrix for standard production for the determination of physiologically occurring analytes, without having to accept potential falsification of the calibration curve steepness or of the calibration curve zero point.

This means that a calibration curve with the correct inclination is only guaranteed when using matrix material which is identical with the material being tested. However, when the selected matrix material itself has an unknown analyte content, the zero point of the calibration curve cannot be determined. It is true that the upward inclination can be determined without knowledge of the position of the calibration curve zero point, but this does not apply to the path of the calibration curve.

It is therefore an object of the invention to make available a process by means of which it is possible to determine the sample blank value in the same matrix as is used for the determination of the analyte. Furthermore, it is an object of the invention to create a process by means of which reproducible calibration curves and therefore exact measurement values can be obtained.

This object is attained by a process for the determination of a reaction partner in an immunological reaction in which the reaction partner to be determined is brought into contact with a labelled specific receptor $R_1$ and with at least one unlabelled receptor $R_2$, and in which one of the unlabelled receptor $R_2$ is bound to a solid phase by a substance $R_3$ which binds to $R_2$, wherein for the determination of the sample blank value, the labelled receptor $R_2$, which is bound to the receptor fixed on the solid phase is replaced by another unmarked receptor $R'_{2'}$ which does not react with the other reaction partner of $R_2$.

In the process according to the invention, for determination of the sample blank value, the same matrix and the same solid phase, including $R_3$, can be used for determination of the analyte. It is possible to dispense with treatment of the matrix for the removal of a possibly present reaction partner to be determined. In this manner it is insured that the blank value and analysis show similar behavior in the selected testing system.

For the determination of a reaction partner of an immunological reaction, i.e., the analyte, the analyte content of a sample is determined by incubating it with a labelled receptor $R_1$ which is specific to the reaction partner, and at least one unlabelled receptor $R_2$. $R_2$ has two reaction partners, namely $R_3$ and either the analyte itself or a further receptor $R_{2a}$ which is capable of binding with the analyte. Moreover, for the determination of the sample blank value a sample from the same origin is also incubated with receptor $R_1$. However, instead of $R_2$, receptor $R'_2$ which does not react with the other reaction partner of $R_2$, i.e., analyte or $R_{2a}$, is added. The determination itself as well as the sample blank value determination can, for example, be carried out so that at first either $R_2$ or $R'_2$ are added, after incubation and washing the sample is added, and after further incubation and washing, $R_1$ is added. Subsequently incubation is carried out, with an optional washing step, and then the determination of the label is effected in either the liquid or solid phase. However, these reaction steps can also be partially or completely performed simultaneously or in reverse sequence. Here, however, attention must be paid to the fact that $R_3$ is present in surplus with respect to $R_2$, so that the reaction partner to be determined is completely bound by $R_2$ to $R_3$. In this way in both batches the unspecific accumulations which are typical of the respective matrix occur, especially of the marked receptor $R_1$ on the solid phase.

However, in the batch for the sample blank value the specific reaction does not take place. Thus for each batch a measurement signal is obtained, said signal being generated by unspecific, so-called matrix effects and being identical in both batches, whereas for the batch for determination of the analyte, the signal is larger by the amount which corresponds to the content of analyte. If a sample with unknown analyte content is measured against this sample blank value, the difference of the two measurement signals can be allocated to the amount of the labelled receptor $R_1$, which is specifically bound by $R_3$ which is fixed on the solid phase. Thus, by comparison of the measurement signals which are obtained during blank sample value measurement and analyte measurement, it is possible to differentiate between the portion to be traced back to unspecific accumulations and the portion which is de facto generated by the reaction partner to be determined.

Within the framework of the invention, preferred receptors are complete antibodies with binding property, antibody fragments or conjugates of antibodies, or antibody fragments with haptens.

As the receptor $R_1$, a labelled receptor is used which is specific for the analyte, i.e., it binds only with the latter. The receptor $R_1$, which is used in a known amount, is labelled in a manner known to the expert. Preferably this labelling is done by coupling with an enzyme, a fluorescent, chemiluminescent or radioactive substance. Processes for the labelling of such receptors are known to the specialist, for example from Clin. Chim. Acta 81: 1–40 (1977), and therefore require no further explanation here.

The receptors $R_2$ and $R'_2$ and optionally $R_{2a}$ can be antibodies, antibody fragments or derivatives thereof. $R_{2a}$ can also be a binding partner of an antibody, for example when the analyte itself is an antibody. Suitable as derivatives are, for example, antibodies or fragments which are coupled to one binding partner of a substance pair capable of binding with each other. In this case, $R_3$ is then the other partner of this substance pair. The following should be named as suitable substance pairs: for example antigen/hapten antibodies, protein A-immunoglobulin G, avidin/biotin, concanavalin A-lectin, DNA-DNA (hybrid).

As $R_2$ and $R'_2$, for example, antibodies or fragments are used which are coupled to a hapten. In this case, $R_3$ is an antibody directed against the hapten. Preferably, receptors $R_2$ and $R'_2$ bind in approximately identical fashion to $R_3$. When using haptenized antibodies or fragments, the degree of haptenization of $R_2$ and $R'_2$ should be comparable or identical.

As the receptor $R'_2$ which is exchanged in the sample blank value with receptor $R_2$, a receptor is used which does not react with the analyte. This receptor $R'_2$ should have no influence on the non-specific binding of the labelled receptor $R_1$ on the solid phase, or should cause no difference in the non-specific bonding the marked receptor $R_1$. Suitability of a receptor $R'_2$ for a certain system can be checked by changing labelled receptor $R_1$ with a similarly labelled $R'_1$ receptor which is not specific for the test and subsequently the measurement signals are compared in the absence and presence of the specific receptor $R_2$ or after the exchange of $R_2$ against a receptor $R'_2$. If the measurement signals are identical within the bounds of the error limits, receptor $R'_2$ is suitable for the process according to the invention.

The receptor $R_2$ or the receptor $R'_2$ is bound by a substance $R_3$ which is itself bound to the solid phase. Suitable binding-capable substances $R_3$ are, for example antibodies or antibody fragments as well as binding partners of the above named substance pairs. When $R_2$ and $R'_2$ are antibodies of the class IgG, $R_3$ can be protein A or an antiimmunoglobulin antibody. If $R_2$ and $R'_2$ are haptenized antibodies, $R_3$ can be an antibody directed against the hapten. If $R_3$ is an anti-immunoglobulin antibody, it must be ensured that $R_1$ does not bind to $R_3$. This can be achieved, for example, by ensuring that $R_2$ and $R_1$ are of different, noncrossreacting species or that another antibody fragment is used for $R_3$ than was used for $R_1$. For example, $R_3$ is an anti-Fc γ antibody, whereas $R_1$ is an antibody fragment such as Fab, Fab', or F(ab')$_2$.

Especially preferred as $R_3$ is an antibody which is only capable of binding with one part of the receptor $R_2$ or $R'_2$, and particular preference is given to an antibody which is capable of binding with the Fc portion of the receptor $R_2$ or $R'_2$. Alternatively an antibody can be used as $R_3$ which can bind with the hapten portion of $R_2$ or $R'_2$, with the Fab portion or with the entire receptor $R_2$ or $R'_2$. The linking of the binding-capable substance $R_3$ which is present in the solid phase on an insoluble carrier material can be carried out according to the conventional methods known to the expert for fixing biologically active proteins on solid carrier substances. Both covalent as well as an adsorptive bonding is suitable. However, it is preferably, because of the higher yield which is attainable and of the simplified modus operandi, to use binding which is solely adsorptive, for example on plastic. Reagent glasses of polystyrol and similar plastics which are coated adsorptively on the inner surface with $R_3$ have been found to be especially suitable.

Moreover, the statements contained in U.S. Pat. No. 4,624,930 apply especially to the selection of the receptor and of the binding capable substance $R_3$ as well as to the implementation of the determination process.

The receptors used can be both polyclonal as well as monoclonal antibodies, when antibodies are used. If the receptor $R_2$ to be replaced in the sample blank value is monoclonal, it is preferable that the receptor $R'_2$ which replaces it should also be monoclonal and of the same species. It is particularly preferred that $R_2$ and $R'_2$ belong to the same sub-class. If the receptor $R_2$ is polyclonal, the unspecific receptor $R'_2$ is also preferably polyclonal and of the same species. It is particularly preferred that $R_2$ and $R'_2$ be as similar as possible with respect to their sub-classes.

Using the inventive process it is also possible to compile a calibration curve for a reaction partner to be determined, the zero point and inclination of which can be exactly determined. For this purpose a sample having an unknown content of analyte is toped up with known amounts of analyte. For various analyte additions, the measurement signal is then determined. At the same time and in the same system a sample blank value is determined. From the values obtained, the calibration curve can then be compiled, the inclination of which is not falsified either by matrix effects or by other effects. In this way, an exactly reproducible calibration curve is obtained. Using this exact calibration curve, it is then possible to determine exactly the concentrations of the analyte by the measurement signals which are obtained for an analyte sample.

A further subject of the present invention is a reagent for determination of a reaction partner in an immunological reaction, containing a binding-capable substance $R_3$ which is bound to a solid phase, at least one unlabelled receptor $R_2$ which is capable of binding with $R_3$ and a further reaction partner, and a marked specific receptor $R_1$, and contains physically separated therefrom a further amount of the binding-capable substance $R_3$ bound on a solid phase, an unlabelled receptor $R'_2$ which does not react with the other reaction partner of $R_2$, and a further amount of marked specific receptor $R_1$.

Preferably the reagent is present in the form of two reaction containers, which contain, respectively, the same solid phase, and the same receptor $R_3$ which is bound on the solid phase wherein the receptor $R_3$ is an anti-Ig-antibody. It is especially preferred that the receptor $R_3$ is already bound to $R_2$, or $R'_2$. Alternatively $R_1$ and $R_2$ or $R'_2$ are premixed and $R_3$ is separate therefrom. All the receptors $R_2$ and $R_1$ can be present dry, dissolved or detachably applied on a solid carrier.

In another preferred embodiment, in which the receptor $R_2$ and $R'_2$ are haptenized, these two receptors are already bound on the solid phase by an antibody directed against the hapten.

The invention makes available a process and a reagent which make it possible to compile a calibration curve for the determination of a reaction partner of an immunological reaction, the zero point of which can be precisely indicated and the inclination of which is not falsified. A further advantage of the inventive process is that when making a parallel measurement of the sample and the sample blank value, the differences in the measurement signal can be allocated to the content of reaction partners to be tested, because by the measurement of the sample blank value, unspecific accumulations can be recognized. In this way it is possible to carry out very assured and correct measurements.

The invention will be explained further by the examples.

EXAMPLE 1

Determination of Thyreotropine (TSH) in Human Sera

1. Preparation of the reagent solutions 1.1 Buffer I: 50 mmole/l potassium-phosphate buffer, pH 6.0, prepared by mixing 50 mmole/l of $K_2HPO_4$ solution and 50 mmole/l of $KH_2PO_4$ solution until a pH value of 6.0 is obtained.

1.2. Buffer: Buffer II is prepared as for buffer I with the difference that it is adjusted to have a pH value of 7.5 the buffer additionally contains 10 g/l of bovine serum albumin and 150 mmole/l of sodium chloride.

1.3. Receptor $R_2$ solution, capable of binding with TSH: As the receptor $R_2$, a monoclonal mouse-anti-TSH-antibody of the sub-class $IgG_1$ is used. The ascites liquid which contains this antibody is mixed with ammonium sulfate to 1.8 M. The precipitate is added to a buffer of 15 mM sodium phosphate, pH 7.0 and 50 mM sodium chloride. The solution thus obtained is subjected to passage over DEAE cellulose. The eluate thus obtained containing the TSH-binding-capable antibody is diluted with buffer II to a protein concentration of 1 μg/ml.

1.4. Receptor $R'_2$ solution, not capable of binding with TSH:

This solution is prepared analogously to the receptor $R_2$ solution capable of binding with TSH (1.3), with the difference that in this case a monoclonal mouse-anti-CEA-antibody of the sub-class $IgG_1$ is used.

1.5. Marked receptor $R_1$ solution:

As the receptor $R_1$, a monoclonal mouse-anti-TSH-antibody is also used which however recognizes a different antigen determinant than receptor $R_2$ recognized. The ascites fluid which contains this antibody is purified as shown under 1.3. The complete antibody is dissociated in the manner taught by R. R. Porter, Biochemistry Journal 73, (1959), page 119 to form a Fab fragment. The Fab fragments thus obtained are coupled according to Ishikawa et al., Journal of Immunoassay, No. 4, (1983), pages 209–327, using beta-galactosidase as label. The receptor 1-solution is diluted in buffer II to a concentration of 500 mU/ml (measured with o-nitrophenyl-beta-galactoside at 37°).

1.6 Receptor $R_3$ Solution:

Sheep anti-mouse-Fcγ-antiserum is mixed with ammonium sulfate to 1.8 M. The precipitate is added to a buffer of 15 mM sodium phosphate, pH 7.0 and 50 mM sodium chloride. The solution thus obtained is subjected to passage over DEAE cellulose. The eluate which contains the specific antibody is diluted in buffer I to a protein concentration of 50 μg/ml.

1.7. Substrate solution:

| | |
|---|---|
| Chlorophenolred-$\beta$-Galactoside (prepared according to U.S. Pat. No. 4,668,622) | 5 mmole/l (3.05 g/l) |
| HEPES | 70 mmole/l (16.7 g/l) |
| Sodium Chloride | 154 mmole/l (9 g/l) |
| Bovine serum albumin | 0.3% (3 g/l) |
| Tween 20 | 0.2% (2 g/l) |
| pH (with NaOH) | 7.25 |

2. Implementation (All incubations are carried out at room temperature)

Microtiter plates (MTP, 96 recesses per plate) of polystyrol are incubated with 300 μl receptor $R_3$ solution for one hour. Then the liquid is discarded. Th residual nonspecific binding positions are separated by incubation for half an hour with 300 μl buffer II solution per cup. Subsequently one half of the microtiter plates are incubated with 200 μl per cup with receptor $R_2$ solution capable of binding with TSH (1.3) (portion A of the MTP) and the other half of the microtiter plates are incubated with receptor $R'_2$ solution which is not capable of binding with TSH (1.4) for one hour (portion B of the MTP). After disposing of the receptor solution in the cups, each cup is washed twice with 300 μl of buffer II.

In the subsequent 18-hours of sample incubation, respectively 200 μl of a sample are placed in cups which contain the antibody capable of binding with TSH (portion A of the MTP) and a further 200 μl are placed in cups which contain the antibody not capable of binding with TSH (portion B of the MTP). After the conclusion of the sample incubation, the samples are discarded and the cups are washed three times with 300 μl of buffer II each time.

Thereafter all the MTP cups are incubated with 200 ul of the marked receptor $R_1$ solution (1.5) for three hours. After disposal of the marked receptor $R_1$ solution and washing three times with 300 μl of buffer II, the substrate reaction is started by the addition of 250 μl substrate solution (1.7). After approximately one hour of incubation time, the color formed by the substrate reaction is detected by measurement using a readily available MPT photometer at 570 nm.

3. Evaluation

For each sample, one extinction from portion A of the (extinction A) and from portion B of the MTP (extinction B) are detected. The difference between the extinctions A and B is to be evaluated for one sample.

Th measurement signal thus obtained, which is specific for TSH is associated with a TSH content on the basis of a calibration curve (see below).

For the compilation of the calibration curve for each MTP, samples with different but known TSH contents are set up. (For this purpose samples with the smallest possible TSH initial content should be used). From the signal increase which is obtained by extension in the sample and from the concentrations of TSH used for extension, a calibration curve is compiled which is extrapolated through the zero point of the diagram. Then, using this calibration curve, the TSH contents of the unknown samples can be detected, taking into consideration the blank value specific to the probe.

In a typical test using the process described the following results were obtained:

| Sample | TSH-additive (uU/ml) | Extinction A (mE)[1] | Ext. B (mE)[2] | Ext. A − Ext. B (mE) | $\Delta$[3] (mE) | TSH ($\mu$U/ml) |
|---|---|---|---|---|---|---|
| 1a | — | 89 | 60 | 29 | — | 0.023 |
| 1a | 0.25 | 396 | 59 | 337 | 308 | 0.271 |
| 1a | 0.5 | 719 | 58 | 661 | 632 | 0.531 |
| 1a | 1.0 | 1336 | 63 | 1273 | 1244 | 1.023 |
| 1b | — | 155 | 102 | 53 | — | 0.043 |
| 1c | — | 759 | 165 | 594 | — | 0.477 |
| 1d | — | 85 | 49 | 36 | — | 0.029 |
| 1e | — | 201 | 63 | 138 | — | 0.111 |
| 1f | — | 64 | 41 | 23 | — | 0.018 |
| 1g | — | 474 | 110 | 412 | — | 0.331 |
| 1h | — | 110 | 62 | 48 | — | 0.039 |
| 1i | — | 173 | 60 | 113 | — | 0.091 |

[1] Extinction using an antibody capable of binding with TSH as receptor $R_2$
[2] Extinction using an antibody not capable of binding with TSH as receptor $R'_2$.
[3] Increase of (extinction A − extinction B) after the addition of TSH in sample 1a.

EXAMPLE 2

Determination of $\alpha$-Fetoprotein (AFP) in Human Sera With Monoclonal Antibodies Example 2 corresponds to example 1 except for the following differences:

(a) As receptor $R_2$, capable of binding with AFP, a monoclonal mouse-anti-AFP-antibody of the sub-class IgG$_{2a}$ is used.

(b) As receptor $R'_2$, not capable of binding with AFP, a monoclonal mouse-anti-ferritin-antibody of the sub-class IgG$_{2a}$ is used.

(c) As receptor $R_1$, a monoclonal mouse-anti-AFP-antibody is used which, however, recognizes a different antigen determinant from that of receptor $R_2$.

(d) The samples are diluted with buffer II 1:5 before determination.

(e) The diluted samples are incubated for one hour in the MTP.

(f) The incubation with the marked receptor $R_1$ solution lasts for one hour.

In a typical test in accordance with the process described, the following results are obtained:

| Sample | AFP-additive (IU/ml) | Extinction A (mE)[1] | Ext. B (mE)[2] | Ext. A − Ext. B (mE) | $\Delta$[3] (mE) | AFP ($\mu$U/ml) |
|---|---|---|---|---|---|---|
| 2a | — | 219 | 17 | 202 | — | 1.7 |
| 2a | 2 | 456 | 17 | 439 | 237 | 3.7 |
| 2a | 6 | 918 | 16 | 902 | 700 | 7.7 |
| 2b | — | 208 | 17 | 191 | | 1.6 |
| 2b | 2 | 465 | 17 | 448 | | 3.8 |
| 2c | — | 143 | 18 | 125 | | 1.1 |
| 2c | 2 | 398 | 19 | 379 | | 3.2 |

| Sample | AFP-additive (IU/ml) | Extinction A (mE)[1] | Ext. B (mE)[2] | Ext. A − Ext. B (mE) | Δ[3] (mE) | AFP (μU/ml) |
| --- | --- | --- | --- | --- | --- | --- |
| 2d | — | 394 | 19 | 375 | | 3.2 |
| 2e | — | 512 | 15 | 497 | | 4.2 |
| 2f | — | 272 | 18 | 254 | | 2.2 |
| 2g | — | 130 | 17 | 113 | | 1.0 |
| 2h | — | 152 | 18 | 134 | | 1.1 |
| 2i | — | 456 | 17 | 439 | | 3.7 |
| 2j | — | 894 | 14 | 880 | | 7.5 |

[1]Extinction when using an antibody capable of binding with AFP as receptor $R_2$.
[2]Extinction when using an antibody not capable of binding with AFP as receptor $R'_2$.
[3]Increase of (extinction A − extinction B after the addition of AFP in sample 2a).

EXAMPLE 3

Determination of α-Fetoprotein (AFP) in Human Sera With Polyclonal Antibodies

Example 3 corresponds to example 2 except for the following differences:

(a) As receptor $R_2$, capable of binding with AFP, a polyconal rabbit-anti-AFP-antiserum was used.

(b) Non-specific rabbit serum was used as receptor $R'_2$, not capable of binding with AFP.

(c) As receptor $R_1$, a polyclonal sheep-anti-AFP-antiserum is used which, however, recognizes a different antigen determinant from that recognized by receptor $R_3$. The preparation of the marked receptor-1-solution is carried out analogously to the actions taken for the monoclonal antibody (see above).

(d) As receptor $R_3$, a polyclonal sheep-anti-rabbit-Fcγ-antiserum is used.

In a typical test in accordance with the process described, the following results were obtained:

| Sample | AFP-additive | Extinction A (mE)[1] | Ext. B (mE)[2] | Ext. A − Ext. B (mE) | Δ[3] | AFP (IU/ml) |
| --- | --- | --- | --- | --- | --- | --- |
| 3a | — | 260 | 130 | 130 | — | 1.9 |
| 3a | 2.0 | 403 | 125 | 278 | 148 | 4.1 |
| 3b | — | 312 | 77 | 235 | — | 3.4 |
| 3b | 2.0 | 435 | 75 | 360 | 125 | 5.3 |
| 3c | — | 296 | 150 | 130 | | 1.9 |
| 3d | — | 328 | 86 | 242 | | 3.5 |
| 3e | — | 257 | 121 | 136 | | 2.0 |

[1]Extinction when using an antibody capable of binding with AFP as receptor $R_2$.
[2]Extinction when using an antibody not capable of binding with AFP as receptor $R'_2$.
[3]Increase of (extinction A − extinction B) after the addition of AFP in samples 3a and 3b. The inclination of the calibration curve was found from the average value of Δ for sample 3a and 3b.

EXAMPLE 4

Determination of TSH

The receptors and the substrate solution which were used are identical with the reagents from example 1, as are the purification steps of the receptors as far as and including the passage over the DEAE cellulose and the synthesis of the marked receptor-1-solution. Using the receptors described, reagent carriers are prepared.

Preparation of Reagent Carriers (1) Reagent carrier 1 (capable of binding with TSH): 40 μl of a solution which contains per liter 100 m mole sodium phosphate pH 7.3 (37° C.), 3 m mole magnesium chloride, 9g sodium chloride, 5g bovine serum albumin, 5 mg anti-TSH-monoclonal antibody from the mouse (receptor $R_2$), 1000 U anti-TSH-antibody-(mouse)-Fab-fragment-beta-galactosidase-conjugate (receptor-$R_1$-solution), activity determined with ortho-nitrophenyl-beta-D-galactoside at 37° C., is dripped on a non-woven fabric which consists of commercial polyester paper. Subsequently it is dried at room temperature. These non-woven fabrics are stored until use at 4° C. and a relative air humidity of 20%.

(2) Reagent carrier 1' (not capable of binding with TSH): the preparation is carried out as for reagent carrier 1, except that instead of the anti-TSH-antibody (receptor $R_2$), an anti-CEA-monoclonal antibody from the mouse (receptor $R'_2$) is used.

(3) Reagent carrier 2: on a cellulose non-woven fabric, in accordance with the bromocyanogen activation process (see DE-OS 17 68 512), sheep-antibodies are fixed against the Fc portion of mouse-antibodies (receptor $R_3$ solution), wherein per g of fiber material, 10 μg antibodies are supplied for fixation. By washing the uncoupled antibodies are removed and the non-woven fabric is protectively dried at room temperature. The storage of the non-woven fabrics thus obtained is carried out in analogously with that of reagent carrier 1.

The determination using these two reagent carriers 1 and 2, or 1' and 2, is carried out with the apparatus for the implementation of analytical determinations (FIG. 1) which is described in U.S. Pat. No. 4,690,889.

This teaches a rotor insertion element for a centrifugal analysis machine, consisting of a mold which contains a sample application chamber which is in connection with a plurality of reagent fields which contain respectively an absorptive carrier material impregnated with a predetermined reagent, having at least 1 mixed valve chamber and a measuring chamber which form together a sample liquid transport route, which leads radially outwards from the radial interior, when the insertion element is secured on the rotor and furthermore, it has at least one other chamber for the accommodation of a liquid and a transport route, which leads from said chamber to the measurement guide and is at least partially identical with the sample liquid transport route. This sample liquid transport route leads from a sample application chamber (P) via a chamber (a) which contains a buffer and is filled with an absorptive material, a chamber (c) and a first valve chamber (Vk1) which is disposed between said chambers a and c to a second valve chamber (Vk2) and from the latter via chamber (b) and then via a collector chamber (AK) to the measuring chamber (K). For the reception of a further liquid, a substrate chamber (PK) is provided designed as a pump chamber, which is in communication via a dosing device consisting of dosing chamber (DK) and capillaries (Kap) and an overflow chamber (UK) with the second valve chamber (Vk2). FIG. 1 shows schematically the rotor insertion element which is used.

For the determination of extinction A (specific measurement signal including sample blank value), reagent carrier 1 and reagent carrier 2 are used, while for the determination of extinction B (sample blank value), reagent carriers 1' and 2 are used.

Reagent carriers 1 or 1' are placed on field c of the rotor insertion element and reagent carrier 2 is placed on field d. 40 μl of concentrated sample are pipetted through an aperture on the upper edge directly onto field a. 270 μl of substrate solution are pipetted into chamber PK. Using a suitable centrifugation program, in which high rpm are alternated with stoppage, the sample and the substrate solution are then transported into the direction of the separation matrix and the cuvette.

In the course of the program, the receptor $R_1$ and $R_2$ or $R'_2$ are eluted by the sample liquid from field c, and subsequently the homogeneous mixture is brought to reaction. On field d, the complexes thus formed are bonded to be receptor $R_3$. The transfer of the sample from field c to field d is performed within a very short time.

The substrate solution is divided by the dosing chamber DK into portions, of which the first is used for washing out surplus and non-complexed conjugate. The beta-galactosidase activity which is bound to d via complex formation is proportional to the amount of TSH contained in the sample or to the sample blank value. This activity is determined by a further substrate portion, the substrate being reacted in a five minutes reaction to colored products. The color formed and the further color development per minute in the liquid phase are measured in the cuvette at 576 nm.

Under these conditions the following results were obtained:

| Sample | TSH-additive ($\mu$U/ml) | Ext. $A^1$ (mE) | Ext. $B^2$ (mE) | Ext. A — Ext. B (mE) | $\Delta^3$ (mE) | [TSH] ($\mu$U/ml) |
|---|---|---|---|---|---|---|
| 4a | — | 599 | 598 | −1 | — | 0.0 |
| 4a | 7 | 1602 | 596 | 1006 | 1007 | 6.6 |
| 4a | 13 | 2716 | 641 | 2075 | 2076 | 13.7 |
| 4b | — | 752 | 766 | −14 | | 0.0 |
| 4c | — | 2465 | 561 | 1904 | | 12.5 |
| 4d | — | 689 | | | | |
| | | | 599 | 90 | | 0.6 |
| 4e | — | 744 | 612 | 132 | | 0.9 |
| 4f | — | 745 | 515 | 230 | | 1.5 |
| 4g | — | 650 | 571 | 79 | | 0.5 |
| 4h | — | 2286 | 558 | 1728 | | 11.4 |

All measurements were carried out at 576 nm with a layer thickness of 0.3 cm and were recalculated to a layer thickness d = 1 cm.
[1]Extinction when using reagent carrier 1 (capable of binding with TSH).
[2]Extinction when using reagent carrier 1' (not capable of binding with TSH).
[3]Increase of (extinction A − extinction B) after the addition of TSH in sample 4a.
*Calibration

EXAMPLE 5

Determination of Monoclonal Anti-AFP-Antibodies

Example 5 corresponds to example 1 except for the following differences:

1. As the receptor $R_3$ solution, a sheep-anti-rabbit-Fc$\gamma$-anti-serum is used.
2. As receptor $R_2$, capable of binding with AFP, a rabbit-anti-AFP-antiserum is used. The purification of the antibody is carried out as for receptor $R_3$.
3. As receptor $R'_2$, not capable of binding with AFP, an unspecific rabbit-serum is used. The purification of the antibody is carried out as for receptor $R_3$.
4. As receptor $R_1$, a sheep-anti-mouse-IgG-antibody is used. The purification is carried out as for receptor $R_3$. The antibodies are coupled with peroxidase from horseradish according to the method of Nakane (see M. B. Wilson, P. K. Nakane "Recent Developments in the Periodate Method of Conjugating Horseradish Peroxidase to Antibodies", 1978, Elsevier, North Holland Biomedical Press, pages 215–244, in "Immunofluorescence and Related Staining Techniques"). The antibody-enzyme-conjugate is adjusted in buffer II to a concentration of 80U/l (measured with Guaiacol and $H_2O_2$ as substrate at 25° C.).
5. After the incubation of the microtiter plate with receptor $R_2$ or receptor $R'_2$ and washing in accordance with example 1, each cup is incubated for one hour with 200 $\mu$l of a solution of 12.5 IU/ml AFP in buffer II. Subsequently it is washed twice with 300 $\mu$l of buffer II.
6. The subsequent incubation with antibody-containing sample solutions amount to one hour.
7. The incubation with marked receptor-1-solution lasts for one hours.
8. As the indicator solution, the following is used:
1.8 mM ABTS ®
(2,2'azino-di-[3-ethylbenzothiazoliumsulfonate])
3.3 mM of sodium perborate in 100 mM phosphate-citrate-buffer, pH 4.4.

The incubation lasts for one hour. The measurement of the color formed is carried out at 405 nm after compensation of the photometer against the substrate blank value.

In a typical test according to the method described, buffer II solutions were reacted with various antibodies in alternating concentrations. The following results were obtained.

| Monoclonal mouse-antibody additive type | amount ($\mu$g/ml) | Ext. A (mE) | Ext. B (mE) | Ext. A − Ext. B (mE) |
|---|---|---|---|---|
| — | — | 258 | 267 | −9 |
| anti-AFP-1* | 0.01 | 442 | 272 | 170 |
| anti-AFP-1 | 0.03 | 518 | 251 | 267 |
| anti-AFP-1 | 0.10 | 589 | 261 | 328 |
| anti-AFP-2* | 0.01 | 321 | 245 | 76 |
| anti-AFP-2 | 0.03 | 416 | 245 | 171 |
| anti-AFP-2 | 0.10 | 471 | 244 | 227 |
| anti-Ferritin | 1.00 | 228 | 248 | −20 |
| anti-CEA | 1.00 | 254 | 257 | −3 |

*Two different monoclonal anti-AFP-antibodies.

I claim:

1. In an immunoassay for the determination of an immunological reaction partner comprising:
   contacting a sample suspected of containing said immunological reaction partner with (1) a labeled receptor $R_1$ specific to said immunological reaction partner and with (2) at least one unlabeled receptor $R_2$ bonded to a solid phase through substance $R_3$, said receptor $R_2$ also being specific to said immunological reaction partner;
   the improvement comprising carrying out a determination of the blank value by replacing $R_2$ by another unlabeled receptor $R'_2$, which does not react with the said immunological reaction partner whereby the determined blank value is used to correct for any non-specific binding.

2. Immunoassay of claim 1, wherein $R_2$ binds to the reaction partner to be determined.

3. Immunoassay of claim 1, wherein $R_2$ binds to a complex of $R_1$ and the reaction partner to be determined.

4. Immunoassay of claim 1, wherein $R_3$ is an anti-Ig antibody which does not bind to $R_1$.

5. Immunoassay of claim 1, wherein $R_2$ and $R'_2$ are monoclonal antibodies of the same subclass.

6. Immunoassay of claim 1, wherein $R_2$ and $R'_2$ are antibodies, each of which is bound to a hapten and $R_3$ is an antibody which specifically binds to said hapten.

7. A kit for the determination of a reaction partner comprising (a) a first composition containing a substance $R_3$ bound to a solid phase, at least one unlabelled receptor $R_2$ which binds to $R_3$ and an additional reaction partner, a labelled receptor $R_2$ which specifically binds to said reaction partner, and (b) a physically separated second composition used for determining a blank value containing a second portion of $R_3$ bound to a solid phase, a second portion of $R_1$, and, an unlabelled receptor $R_2$ which reacts with $R_3$ but not the further reaction partner of $R_2$.

8. The kit of claim 7, wherein $R_2$ and $R_2'$ are bound to a solid phase by an anti-Ig antibody.

9. The kit of claim 7, wherein $R_2$ and $R_2'$ are antibodies bound to a solid phase by an antibody specific for said hapten.

* * * * *